United States Patent
Fujita et al.

(10) Patent No.: US 11,971,427 B2
(45) Date of Patent: Apr. 30, 2024

(54) BUBBLE DETECTION IN AN AUTOMATED ANALYSIS DEVICE

(71) Applicant: HITACHI HIGH-TECH CORPORATION, Tokyo (JP)

(72) Inventors: Akinao Fujita, Tokyo (JP); Takushi Miyakawa, Tokyo (JP); Tetsuji Kawahara, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 124 days.

(21) Appl. No.: 17/442,689

(22) PCT Filed: Mar. 10, 2020

(86) PCT No.: PCT/JP2020/010158
§ 371 (c)(1),
(2) Date: Sep. 24, 2021

(87) PCT Pub. No.: WO2020/217750
PCT Pub. Date: Oct. 29, 2020

(65) Prior Publication Data
US 2022/0120774 A1    Apr. 21, 2022

(30) Foreign Application Priority Data
Apr. 26, 2019    (JP) .................................. 2019-085894

(51) Int. Cl.
*G01N 35/10*    (2006.01)
*G01N 27/333*    (2006.01)
(Continued)

(52) U.S. Cl.
CPC ....... *G01N 35/1009* (2013.01); *G01N 27/333* (2013.01); *G01N 33/49* (2013.01);
(Continued)

(58) Field of Classification Search
CPC .. G01N 35/1099; G01N 27/333; G01N 33/49; G01N 33/493; G01N 35/1002; G01N 2035/1062
(Continued)

(56) References Cited

U.S. PATENT DOCUMENTS 3,804,593 A * 4/1974 Smythe .................. G01N 35/08
422/82
4,419,903 A * 12/1983 Jackson ................. G01N 35/08
250/573
(Continued)

FOREIGN PATENT DOCUMENTS

EP    1607747 A2    12/2005
EP    1 756 530    2/2007
(Continued)

OTHER PUBLICATIONS

Extended European Search Report received in corresponding European Application No. 20794243.4 dated Dec. 9, 2022.
(Continued)

*Primary Examiner* — Arlen Soderquist
(74) *Attorney, Agent, or Firm* — MATTINGLY & MALUR, PC

(57) ABSTRACT

Provided is an automated analysis device capable of a more accurate determination of the sizes of bubbles included in a liquid. The automated analysis device includes a detection unit which detects bubbles included in a liquid, an internal standard solution syringe which executes a first liquid supply operation in which a liquid is supplied via the detection unit, a diluent syringe, a sipper syringe, solenoid valves, and a control device which determines whether the size of the bubbles detected during the first liquid supply operation is normal or not based on the operation speed of the liquid
(Continued)

supply unit, and controls the operation of the liquid supply unit according to the determination.

6 Claims, 6 Drawing Sheets

(51) Int. Cl.
  *G01N 33/49*     (2006.01)
  *G01N 33/493*    (2006.01)
(52) U.S. Cl.
  CPC ....... *G01N 33/493* (2013.01); *G01N 35/1002* (2013.01); *G01N 2035/1062* (2013.01)
(58) Field of Classification Search
  USPC .......................................................... 436/43
  See application file for complete search history.

(56) References Cited

U.S. PATENT DOCUMENTS

| | | | | |
|---|---|---|---|---|
| 4,496,346 A * | 1/1985 | Mosteller | .............. | A61M 5/365 604/245 |
| 4,565,500 A * | 1/1986 | Jeensalute | .............. | A61M 5/365 417/63 |
| 4,649,028 A * | 3/1987 | Kaltenbach | ........ | G01N 35/1097 137/625.13 |
| 4,859,864 A * | 8/1989 | Smith | .................... | G01N 21/43 250/577 |
| 5,284,568 A * | 2/1994 | Pace | .................... | G01N 27/403 204/403.03 |
| 6,063,635 A * | 5/2000 | Ohta | ...................... | G01N 35/10 422/549 |
| 6,250,130 B1 * | 6/2001 | Howard | ................ | G01F 1/7086 73/1.16 |
| 6,457,346 B1 * | 10/2002 | Kline-Schoder | ..... | G01N 29/036 73/19.1 |
| 7,792,647 B1 * | 9/2010 | Ding | ...................... | G01B 13/00 222/61 |
| 8,489,341 B2 * | 7/2013 | Brown | .................... | G01F 1/712 702/50 |
| 2004/0105784 A1 * | 6/2004 | Fukuju | ...................... | B01L 9/06 422/68.1 |
| 2007/0191990 A1 | 8/2007 | Duan et al. | | |
| 2009/0319204 A1 * | 12/2009 | Brown | .................... | G01F 1/712 702/47 |
| 2010/0216223 A1 * | 8/2010 | Nakanishi | .......... | G01N 35/1002 422/537 |
| 2021/0318260 A1 * | 10/2021 | Ozawa | ................ | G01N 27/4163 |

FOREIGN PATENT DOCUMENTS

| | | |
|---|---|---|
| JP | 2006-4831 A | 1/2006 |
| JP | 2007-245038 A | 9/2007 |
| WO | 2013/042551 A1 | 3/2013 |

OTHER PUBLICATIONS

International Search Report of PCT/JP2020/010158 dated Jun. 9, 2020.
Chinese Office Action received in corresponding Chinese Application No. 202080018701.1 dated Dec. 6, 2023.
European Office Action received in corresponding European Application No. 20 794 243.4 dated Mar. 6, 2024.

* cited by examiner

[FIG. 1]
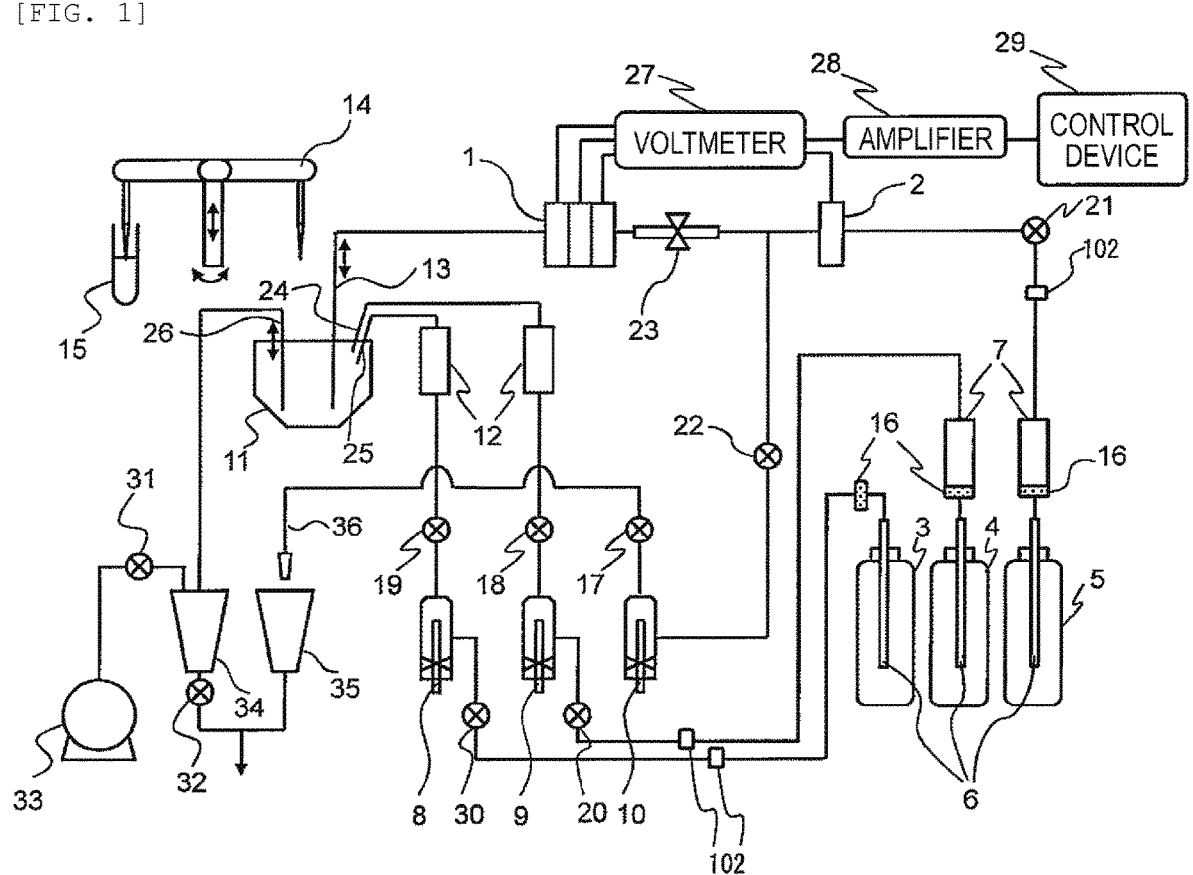

[FIG. 2]
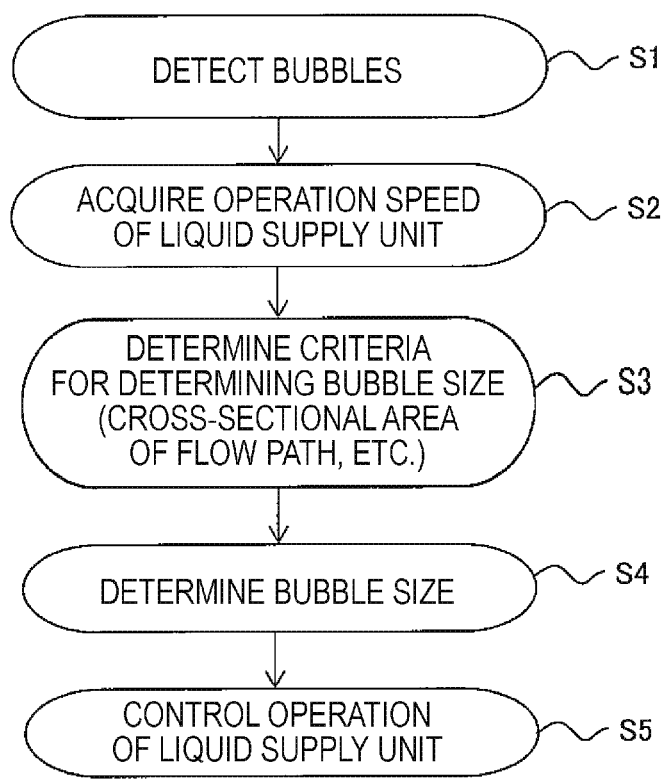

[FIG. 3]
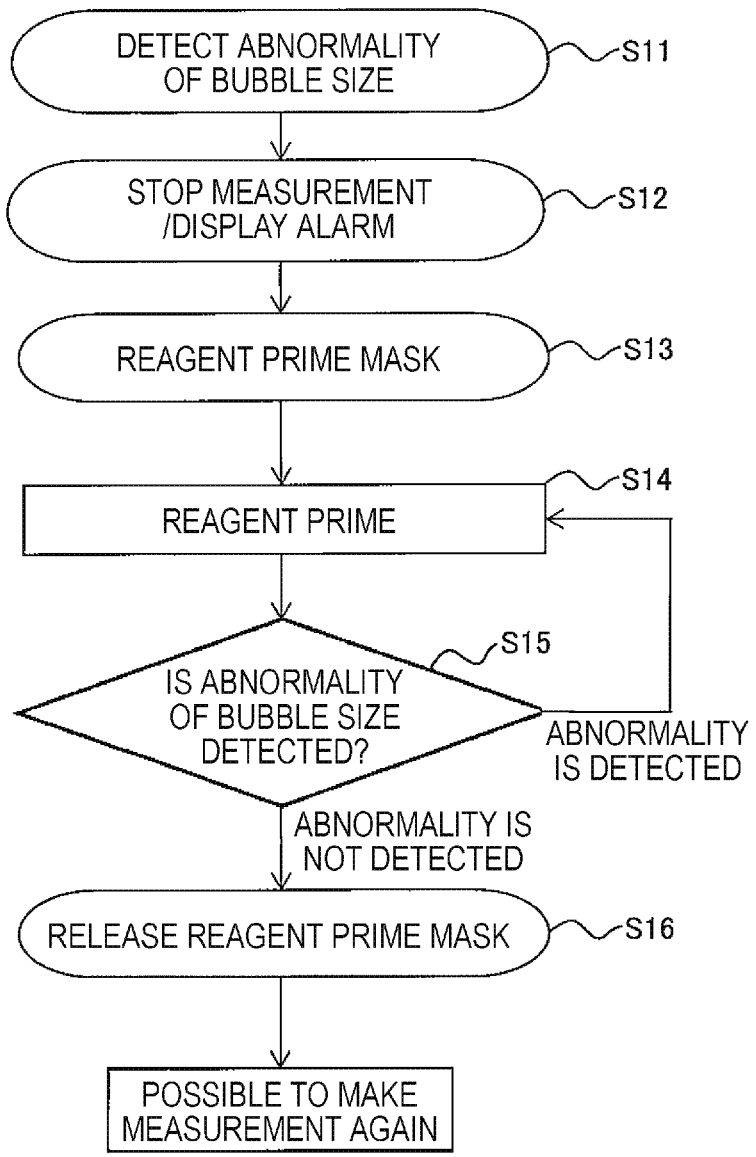

[FIG. 4]
(A)
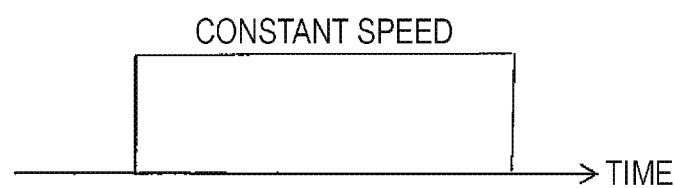
(B)
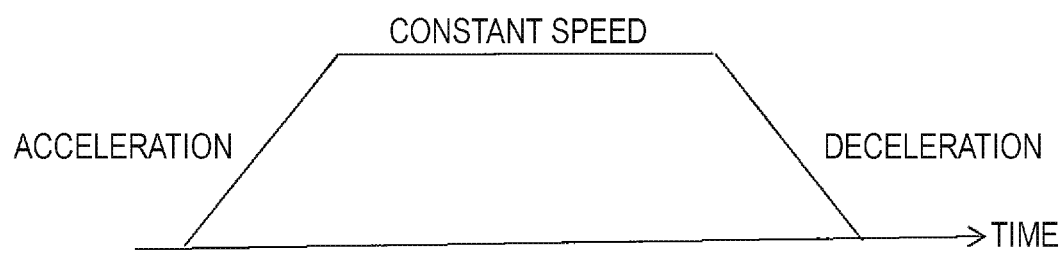

[FIG. 5]
(A)
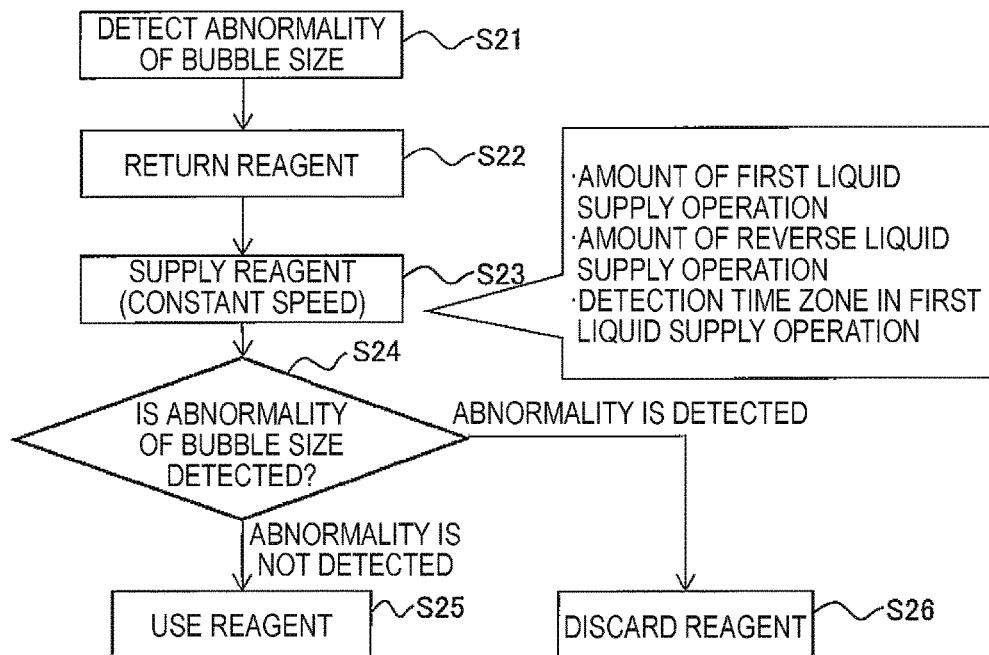
(B)
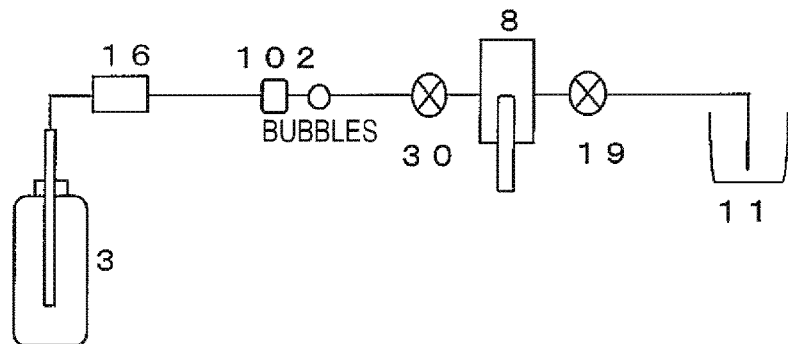
(C)
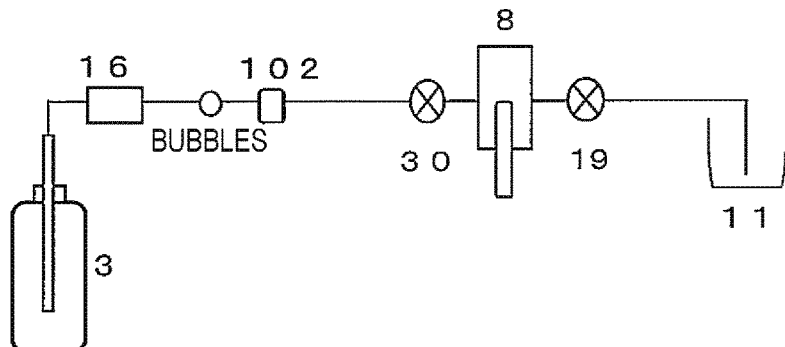

[FIG. 6]
(A)
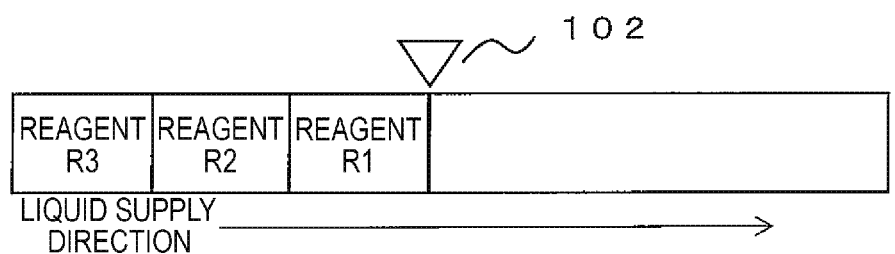
(B)
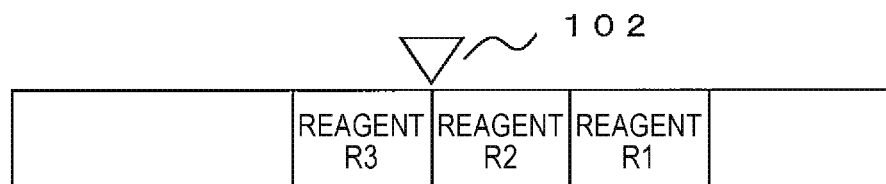
(C)
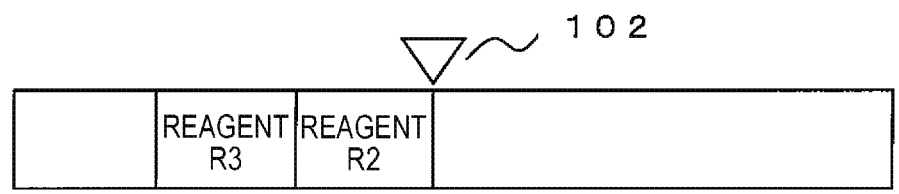
(D)
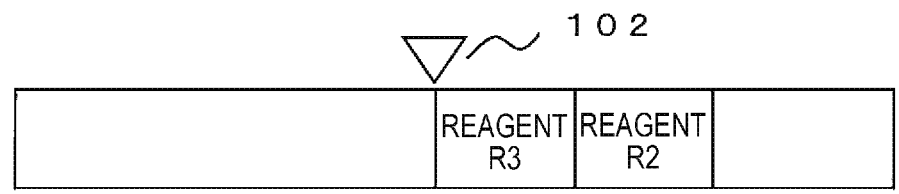

BUBBLE DETECTION IN AN AUTOMATED ANALYSIS DEVICE

TECHNICAL FIELD

The present invention relates to an automated analysis device, for example, an electrolyte analysis device.

BACKGROUND ART

There is an electrolyte analysis device as a kind of automated analysis device. The electrolyte analysis device is a device that measures the concentration of a specific electrolyte contained in an electrolyte solution such as blood or urine of a human body and measures the concentration using an ion-selective electrode. As a general measuring method, an ion-selective electrode is supplied with serum directly as an electrolyte solution or with a sample solution obtained by diluting serum with a diluent. Then, the liquid-liquid potential between the ion-selective electrode and the reference electrode solution is measured. Next (or before the measurement), a standard solution is supplied to the ion-selective electrode, the liquid-liquid potential with the reference electrode solution is measured in the same manner, and the electrolyte concentration of the sample solution is calculated from the two liquid-liquid potential levels.

In such a flow-type electrolyte analysis device, reagents such as a diluent, a standard solution, and a reference electrode solution are used as consumables, and the amount of those reagents used in one analysis is determined by the parameters freely set.

In particular, for the diluent that dilutes the sample, the accuracy of the amount used is important because the dilution ratio with the sample affects the measurement result of the electrolyte. For example, if the gas dissolved in the reagent foams in the flow path, the sample will be diluted by the amount of foaming, which is less than the amount of reagent actually required, and it may not be possible to calculate a normal measurement result. Further, when re-analysis is required for this purpose, it is necessary to re-obtain a specimen from the patient for the re-analysis, which may increase the burden on the patient. Therefore, it is desirable to calculate a normal measurement result. For that purpose, it is desirable to perform the analysis without using a reagent incorporated with bubbles, determine whether the bubble size affects the measurement result, and perform the analysis after determining whether or not the reagent can be used.

JP-A-2007-245038 (PTL 1) discloses a bubble removing device as a measure for removing bubbles incorporated or generated, the device having a function of analyzing an image of a flow path with a microscope provided in the device, determining whether or not bubbles are present in the flow path, comparing with the shapes of bubbles whose dimension and shape have been stored in the control device in advance in a timely manner, and determining the presence or absence of bubbles, and having a function of discharging bubbles by pressure fluctuation.

CITATION LIST

Patent Literature

PTL 1: JP-A-2007-245038

SUMMARY OF INVENTION

Technical Problem

However, with the technology of the related art, there is a problem that it is difficult to accurately determine the sizes of bubbles.

For example, in the bubble removing device of PTL 1, in order to determine the sizes of bubbles incorporated or generated in the flow path, a comparison is made with images of bubbles registered in advance. However, since it is difficult to generate any bubbles in a normal size used for the image to be registered in advance and it is not easy to generate bubbles in a desired appropriate size, the method of comparing with the image is not easy.

The present invention has been made to solve such a problem and an object of the present invention is to provide an automated analysis device capable of more easily and accurately determining the sizes of bubbles contained in a liquid.

Solution to Problem

The automated analysis device according to the present invention includes
a detection unit which detects bubbles included in a liquid;
a liquid supply unit which executes a first liquid supply operation in which the liquid is supplied via the detection unit;
a determination unit which determines whether the bubble size detected during the first liquid supply operation is normal or not based on the operation speed of the liquid supply unit; and
a control unit which controls the operation of the liquid supply unit according to the determination of the determination unit.

This specification includes the disclosure of Japanese Patent Application No. 2019-085894, which is the basis of the priority of the present application.

Advantageous Effects of Invention

According to the automated analysis device according to the present invention, the sizes of bubbles contained in a liquid can be determined more easily and accurately. For example, the sizes of bubbles can be determined without comparison with a pre-registered image.

BRIEF DESCRIPTION OF DRAWINGS

FIG. 1 is an overall diagram schematically illustrating an electrolyte analysis device according to Example 1.

FIG. 2 is a flow chart illustrating a flow of the operation in which the electrolyte analysis device of FIG. 1 determines the sizes of bubbles.

FIG. 3 is a flow chart illustrating a flow of the operation executed when it is determined that the size of bubbles detected during a first liquid supply operation is abnormal.

FIG. 4 is a diagram illustrating an example of the operation speed of a liquid supply unit according to Example 2.

FIG. 5 is a diagram illustrating an operation of the electrolyte analysis device according to Example 2.

FIG. 6 is a diagram schematically illustrating the movement of a liquid according to Example 3.

DESCRIPTION OF EMBODIMENTS

Hereinafter, embodiments of the present invention will be described with reference to the accompanying drawings.

Example 1

FIG. 1 is an overall schematic diagram of an electrolyte analysis device according to Example 1. The electrolyte analysis device of the present example is configured as an automated analysis device or apart thereof. Examples of such an automated analysis device include a biochemical automated analysis device, an automated immunoanalysis device, and the like. Alternatively, the automated analysis device may be a mass spectrometer used for clinical examination, a coagulation analysis device for measuring the coagulation time of blood or the like. Alternatively, the automated analysis device may be a composite system of amass spectrometer or a coagulation analysis device and a biochemical automated analysis device or an automated immunoanalysis device or may be an automated analysis system to which these are applied.

The electrolyte analysis device shown in FIG. 1 is a flow-type electrolyte analysis device using an ion-selective electrode (hereinafter, ISE electrode). FIG. 1 shows five main mechanisms of the electrolyte analysis device: a sample dispensing unit, an ISE electrode unit, a reagent unit, a liquid supply unit, and a waste liquid mechanism; and shows a control device 29 (control unit) that controls the above and performs the calculation of the electrolyte concentration with the measurement result and the display thereof.

The sample dispensing unit includes a sample probe 14 and a sample container 15. The sample probe 14 dispenses the sample (a specimen of a patient, etc.) held in the sample container 15 and draws the sample into the automated analysis device. Here, the specimen is a general term for an analysis target collected from a patient's living body, and is, for example, blood or urine. In addition, the specimen may be obtained by pretreatment of the analysis targets.

The ISE electrode unit includes a dilution tank 11, a sipper nozzle 13, a diluent nozzle 24, an internal standard solution nozzle 25, an ISE electrode 1, a reference electrode 2, a pinch valve 23, a voltmeter 27, and an amplifier 28. The sample dispensed in the sample dispensing unit is discharged to the dilution tank 11, diluted by the diluent discharged from the diluent nozzle 24 into the dilution tank 11, and stirred. The sipper nozzle 13 is connected to the ISE electrode 1 through a flow path, and the diluted sample solution sucked from the dilution tank 11 is sent to the ISE electrode 1 through the flow path.

On the other hand, the reference electrode solution contained in a reference electrode solution bottle 5 is sent to the reference electrode 2 by operating a sipper syringe 10 with the pinch valve 23 closed. After that, when the pinch valve 23 is opened, the diluted sample solution sent to the ISE electrode flow path and the reference electrode solution sent to the reference electrode flow path come into contact with each other and the ISE electrode 1 is electrically conducted with the reference electrode 2. The ISE electrode unit measures the concentration of a specific electrolyte contained in the sample based on the potential difference (liquid-liquid potential) between the ISE electrode 1 and the reference electrode 2.

As a specific example, the ISE electrode 1 is attached with an ion-sensitive film having a property that the electromotive force changes according to the concentration of specific ions (for example, sodium ion ($Na^+$), potassium ion ($K^+$), chloride ion ($Cl^-$), etc.) in the sample solution. As a result, the ISE electrode 1 outputs an electromotive force corresponding to each ion concentration in the sample solution, and the voltmeter 27 and the amplifier 28 acquire the electromotive force between the ISE electrode 1 and the reference electrode 2. The control device 29 calculates and outputs (for example, displays) the ion concentration in the specimen from the acquired electromotive force for each ion. The sample solution remaining in the dilution tank 11 is discharged by a waste liquid mechanism described later.

The reagent unit includes a suction nozzle 6 that sucks the reagent from the reagent container and supplies the reagent necessary for measurement. Further, the reagent unit may include a degassing mechanism 7 and a filter 16. When measuring electrolytes, three types of liquids of an internal standard solution, a diluent, and a reference electrode solution are used as reagents, and the reagent unit is set with an internal standard solution bottle 3 as a reagent container for containing the internal standard solution, a diluent bottle 4 for containing the diluent, and the reference electrode solution bottle 5 for containing the reference electrode solution. FIG. 1 shows this state. Further, when cleaning the device, a cleaning liquid bottle for storing the cleaning liquid may be set in the reagent unit.

The internal standard solution bottle 3 and the diluent bottle 4 are connected to the internal standard solution nozzle 25 and the diluent nozzle 24 through a flow path via the filter 16, respectively, and each nozzle is installed in the dilution tank 11 with the tip thereof introduced. Further, the reference electrode solution bottle 5 is connected to the reference electrode 2 through a flow path via the filter 16. A degassing mechanism 7 is connected to the flow path between the diluent bottle 4 and the dilution tank 11 and the flow path between the reference electrode solution bottle 5 and the reference electrode 2, respectively, and a degassed reagent is supplied into the dilution tank 11 and the reference electrode 2.

The degassing mechanism 7 is a mechanism for preventing the bubbles from being directly supplied to the dilution tank 11 and the reference electrode 2 when bubbles appear in the reagent. In each syringe (described later) of the liquid supply unit, in order to make the flow path set to negative pressure and suck up the reagent from each bottle, the gas dissolved in the reagent may appear as bubbles in the reagent, but the degassing mechanism 7 prevents, to some extent, the situation where the reagent having bubbles contained therein is supplied to the dilution tank 11 or the reference electrode 2.

The liquid supply unit includes an internal standard solution syringe 8, a diluent syringe 9, a sipper syringe 10, and solenoid valves 17, 18, 19, 20, 21, 22, and 30, and takes charge of the operation of liquid supply within or between the mechanisms. Further, the liquid supply unit may include a preheat 12. For example, the internal standard solution and the diluent are sent to the dilution tank 11 by the operation of the internal standard solution syringe 8 and the diluent syringe 9, and the corresponding solenoid valves provided in the flow path, respectively. The preheat 12 reduces the influence of the temperature on the ISE electrode 1 by controlling the temperatures of the internal standard solution and the diluent reaching the ISE electrode 1 within a certain range.

The waste liquid mechanism includes a first waste liquid nozzle 26, a second waste liquid nozzle 36, a vacuum bottle 34, a waste liquid receiver 35, a vacuum pump 33, and solenoid valves 31 and 32, and discharges the sample solution remaining in the dilution tank 11 and the reaction solution remaining in the flow path of the ISE electrode unit.

As an operation example of the electrolyte analysis device shown in FIG. 1, the operation of measuring the electrolyte concentration will be described. The measurement operation is controlled by the control device 29.

First, the sample dispensed from the sample container 15 by the sample probe 14 of the sample dispensing unit is discharged to the dilution tank 11 of the ISE electrode unit. After that, the diluent is discharged from the diluent bottle 4 to the dilution tank 11 via the diluent nozzle 24 by the operation of the liquid supply unit (particularly, the diluent syringe 9). In the dilution tank 11, the sample is diluted with the diluent. As described above, in order to prevent bubbles from being generated due to changes in the temperature and pressure of the diluent in the flow path, the degassing mechanism 7 installed in the middle of the diluent flow path may perform the degassing process. The diluted sample solution is sucked into the ISE electrode 1 by the operation of the liquid supply unit (particularly, the sipper syringe 10 and the solenoid valve 22).

On the other hand, the reference electrode solution is sent from the reference electrode solution bottle 5 to the reference electrode 2 by the operation of the liquid supply unit (particularly, the pinch valve 23 and the sipper syringe 10). The reference electrode solution is, for example, an aqueous solution of potassium chloride (KCl) having a predetermined concentration. After the reference electrode solution is sent, the pinch valve 23 is opened and the sample solution and the reference electrode solution come into contact with each other, and thus, the ISE electrode 1 and the reference electrode 2 are electrically conducted with each other. The ISE electrode potential (liquid-liquid potential) based on the reference electrode potential is measured using the voltmeter 27 and the amplifier 28.

It is desirable to increase the electrolyte concentration of the reference electrode solution in order to reduce the influence of concentration fluctuations while the sample solution is being sent. On the other hand, near the saturation concentration, there is a possibility to be crystallized and cause clogging of the flow path. Considering these comprehensively, it may be desirable that the electrolyte concentration of the reference electrode solution is between 0.5 mmol/L and 3.0 mmol/L.

Further, before or after the measurement using the sample solution, the internal standard solution of the internal standard solution bottle 3 set in the reagent unit is discharged to the dilution tank 11 by the internal standard solution syringe 8 and the electrolyte concentration of the internal standard solution is measured in the same manner as the measurement using the sample solution.

The control device 29 performs a calculation using the ISE electrode potential measured for the sample solution and calculates the electrolyte concentration in the sample solution. At this time, a more accurate measurement of the electrolyte concentration can be performed by performing calibration based on the measured ISE electrode potential of the internal standard solution. Specific calculation contents of the calibration process can be appropriately designed by those skilled in the art based on known techniques and the like.

The control device 29 can be configured as a computer including a calculation unit such as a central processing unit (CPU), a storage unit such as a random access memory (RAM), and an input and output unit such as an I/O port. The storage unit and the input and output unit are configured so that data can be exchanged with the calculation unit via an internal bus or the like. The input and output unit are connected to the above-described mechanisms of the electrolyte analysis device, and the control device 29 controls the operation of each mechanism via the input and output unit.

The storage unit may store a program that defines the operation of the electrolyte analysis device and the control device 29 may control the operation of the electrolyte analysis device by executing the program. The program is read into the storage unit and executed by the calculation unit. Further, an input and output device may be connected to the control device 29 and the electrolyte analysis device may perform the input from the user or the display of the measurement result via the input and output device.

Next, the detection unit that detects bubbles in the electrolyte analysis device of the present example will be described. The detection unit of the present example is configured as a detector 102 shown in FIG. 1. The detector 102 is provided in each of a flow path connecting the internal standard solution bottle 3 and the dilution tank 11, a flow path connecting the diluent bottle 4 and the dilution tank 11, and a flow path connecting the reference electrode solution bottle 5 and the reference electrode 2. When the degassing mechanism 7 or the filter 16 is provided in the flow path, the detector 102 may be provided on the downstream side of the degassing mechanism 7 or the filter 16.

As described above, in order to prevent bubbles from being generated due to changes in the temperature and pressure of the diluent in the flow path, the degassing mechanism 7 installed in the middle of the diluent flow path may perform the degassing process. Even in such a case, it is assumed that not all gases can be removed. In such a case, the detector 102 is provided so as to be able to detect bubbles that cannot be completely removed by the degassing mechanism 7.

In the flow path through which the liquid passes, the detector 102 can detect bubbles contained in the liquid passing through the flow path. The specific configuration of the detector 102 is arbitrary and can be appropriately designed by those skilled in the art based on known techniques, but in the present example, the configuration is an optical type. For example, the detector detects the wavelength of light (or generally, electromagnetic waves) that passes through the flow path, converts the detected wavelength into an electric signal, and outputs the signal. Here, in general, the wavelength of light changes between the state where the inside of the flow path is filled with liquid and the state where bubbles are incorporated, and thus, bubbles can be detected based on the difference in wavelength.

The determination unit of the electrolyte analysis device (not shown, for example, configured in the control device 29 corresponding to each of the detectors 102) receives the electric signal, and based on this, whether the bubble size is normal or not is determined. If the detector 102 does not detect bubbles or if the detector 102 detects bubbles but the bubble size is less than the reference value, it is determined that the bubble size is normal. On the other hand, when the detector 102 detects bubbles and the bubble size is equal to or larger than the reference value, it is determined that the bubble size is not normal (or abnormal).

The method of determining the bubble size can be appropriately designed by those skilled in the art, and for example, a determination method based on the detection time is possible. As a specific example, when the detector 102 detects bubbles for a time equal to or longer than a predetermined threshold time in a predetermined detection time zone, it is determined that the bubble size is equal to or larger than the reference value. On the other hand, if the detector 102 does not detect bubbles or the time when the bubbles are detected is less than the threshold time in the predetermined detection time zone, it is determined that the bubble size is less than the reference value. The threshold time can be set in the control device 29 as a parameter representing the threshold and the bubble size can be determined based on the parameter.

Further, the control device 29 can control the operation speed of the liquid supply unit. For example, the operation speeds of the internal standard solution syringe 8, the diluent syringe 9, and the sipper syringe 10 can be individually controlled. Here, since the moving speed of bubbles in the flow path depends on the flow velocity, the control device 29 changes the threshold time according to the operation speed of the liquid supply unit. The operation speed is expressed, for example, in volume/hour (for example, the value obtained by dividing the volume of liquid with time) but may use distance/time (for example, the value obtained by dividing the moving distance of a syringe with time) or a value in another unit.

For example, the threshold time can be set to T1 seconds when the liquid supply unit is performing a predetermined high-speed operation, and the threshold time can be set to T2 seconds when the liquid supply unit is performing a predetermined low-speed operation (where T1<T2). Alternatively, the threshold time can be set to T3 seconds when the operation speed of the liquid supply unit is within a first range, and the threshold time can be set to T4 seconds when the operation speed is within a second range on the side slower than the first range (where T3<T4).

Further, as a function expressing the threshold time, a function having the operation speed of the liquid supply unit as a variable may be defined in the storage unit. In that case, the threshold time can be calculated by substituting the operation speed at any time into this function. As a specific example, a function that is inversely proportional to the operation speed can be used.

The threshold time may be further changed based on the cross-sectional area of each flow path through which each liquid passes. A person skilled in the art can appropriately determine the strict definition of "cross-sectional area of the flow path". For example, when the cross section of the flow path is circular, the cross-sectional area is proportional to the square of the inner diameter, and thus, the cross-sectional area can be represented by the inner diameter. Further, when the cross-sectional area of the flow path is not constant, the cross-sectional area of the portion having the smallest cross-sectional area can be used.

A person skilled in the art can appropriately design the relationship between the cross-sectional area and the threshold time. As an example of expressing the above-mentioned operation speed in terms of volume/time, the threshold time is used as it is if the inner diameter of the flow path has a predetermined value (for example, 1.0 mm), and a value corrected to shorten the threshold time can be used if the inner diameter of the flow path has a larger value (for example, 1.5 mm). By using the cross-sectional area in this way, it becomes possible to determine the bubble size more appropriately.

FIG. 2 is a flowchart showing a flow of operation in which the electrolyte analysis device according to the present example determines the sizes of bubbles. This operation is executed, for example, while the liquid supply unit is executing the operation of feeding the liquid via the detector 102 in the flow path (first liquid supply operation).

The operation of FIG. 2 is started in response to the detector 102 detecting bubbles contained in the liquid passing through the flow path during the first liquid supply operation (step S1). The determination unit acquires the operation speed of the corresponding liquid supply unit (step S2). For example, the determination unit related to the detector 102 provided in the flow path from the internal standard solution bottle 3 acquires the operation speed of the internal standard solution syringe 8.

Next, the determination unit determines the determination criteria for determining the sizes of the bubbles (step S3). A determination criterion is the threshold time that is changed based on the operation speed of the liquid supply unit in the above example. Further, the threshold time may be changed based on the cross-sectional area of the flow path as described above. In that case, the control device 29 may store a value representing the cross-sectional area of the flow path corresponding to each liquid and may execute a process of appropriately acquiring this value.

Next, the determination unit determines whether or not the detected bubble size is normal based on the operation speed of the liquid supply unit (step S4). For example, the time during which the detector 102 detected bubbles in step S1 is compared with the threshold time acquired in step S3, and if the time during which bubbles were detected is less than the threshold time, it is determined that the bubble size is normal. If the time during which the bubbles were detected is equal to or longer than the threshold time, it is determined that the bubble size is not normal (or abnormal).

Next, the control device 29 controls the operation of the liquid supply unit according to the determination of the determination unit in step S4 (step S5). As an example, FIG. 3 shows an example of control when the bubble size is determined to be abnormal.

FIG. 3 is a flowchart showing the flow of the operation executed when the bubble size detected during the first liquid supply operation is determined to be abnormal. If the analysis operation is continued while the bubble size is abnormal, the analysis result may be affected. The operation of FIG. 3 is an operation for avoiding such a situation.

When the bubble size is determined to be abnormal (step S11), the measurement operation is stopped and an alarm is displayed on a display unit (not shown) provided in the control device 29 (step S12).

Next, a reagent prime mask is set to perform the reagent prime operation (step S13). The setting of the reagent prime mask can be performed by any method and may be performed using, for example, a specific state variable or flag stored in the storage unit of the control device 29. The control device 29 does not measure the liquid-liquid potential when the reagent prime mask is set. By setting the reagent prime mask in this way, improper measurement without performing reagent prime is prevented.

Next, reagent prime is executed in order to discharge the bubbles in the flow path in which the bubbles have been detected (step S14). By discharging the bubbles in the flow path by the reagent prime, the analysis operation can be performed again.

The specific operation of the reagent prime can be designed freely and an example will be described below. For example, when the reagent of the internal standard solution is primed, the internal standard solution is discharged to the dilution tank 11 using the internal standard solution syringe 8. After that, the internal standard solution in the dilution tank 11 is sucked by the vacuum pump 33 through the first waste liquid nozzle 26 to be discarded. By repeating this a plurality of times, the reagent in the entire flow path can be replaced with a new reagent.

Similarly, when the reagent of the diluent is primed, the internal standard solution is discharged to the dilution tank 11 using the diluent syringe 9. After that, the diluent in the dilution tank 11 is sucked by the vacuum pump 33 through the first waste liquid nozzle 26 to be discarded. By repeating this a plurality of times, the reagent in the entire flow path can be replaced with a new reagent.

When the reagent of the reference electrode solution is primed, the pinch valve 23 is closed, the solenoid valve 22 is opened, and then the reference electrode solution is drained to the waste liquid receiver 35 using the sipper syringe 10. By repeating this a plurality of times, the reagent in the entire flow path can be replaced with a new reagent.

It is confirmed that bubbles of abnormal sizes are not incorporated even when the reagent prime is executed (step S15). This confirmation may be performed by the operation shown in FIG. 2 in the same manner as the first liquid supply operation described above or may be performed in another method. If no bubbles are detected during reagent prime or if the bubble size is normal, the reagent prime mask is released (step S16). This makes it possible to measure again. If the bubble size detected during the reagent prime is abnormal, the operation returns to step S14 and the reagent prime is executed again.

As described above, according to the electrolyte analysis device according to Example 1, the sizes of bubbles contained in the liquid can be determined more easily and accurately. For example, the sizes of bubbles can be determined without comparison with a pre-registered image.

Example 2

In Example 2, Example 1 is modified so that when an abnormality in the bubble size is detected, a more accurate determination operation is additionally executed.

FIG. 4 shows an example of the operation speed of the liquid supply unit (for example, the operation speed of the syringe). The operation speeds of the internal standard solution syringe 8, the diluent syringe 9, and the sipper syringe 10 can be set arbitrarily, and for example, it is possible to be designed to operate at a constant speed as shown in FIG. 4A and it is also possible to be designed to operate while changing the operation speed as shown in FIG. 4B. In the example of FIG. 4B, after the acceleration operation, the operation shifts to the constant speed operation, then to the deceleration operation, and to the stop.

In the example of FIG. 4B, the load on the mechanical element (motor and the like) is smaller than that of the example of FIG. 4A and for example, step-out of the motor is less likely to occur. On the other hand, in the example of FIG. 4B, when bubbles pass through the detector 102 during the acceleration operation or the deceleration operation, the detection result may not be stable because the flow velocity changes. For example, there may be a discrepancy between the operation speed acquired in step S2 and the actual operation speed and the bubble size may be erroneously determined to be greater than or equal to the threshold value even if the bubble size is actually less than the threshold value. Or, conversely, even if the bubble size is actually greater than or equal to the threshold value, the bubble size may be erroneously determined to be less than the threshold value.

Further, even in the constant speed operation as shown in FIG. 4A, the flow velocity at the start of the operation (or immediately after the start of the operation) and at the end of the operation (or immediately before the end of the operation) remains unstable and is not necessarily in the constant speed state. Therefore, the detection result may not be stable. For example, depending on the operation timing of the syringe, even if the bubble size is actually less than the threshold value, the bubble size may be erroneously determined to be greater than or equal to the threshold value. Or, conversely, even if the bubble size is actually greater than or equal to the threshold value, the bubble size may be erroneously determined to be less than the threshold value.

It is preferable to avoid such an erroneous determination because such an erroneous determination leads to unnecessary interruption of the measurement operation and deterioration of the measurement accuracy. The present example is configured to reduce such an erroneous determination and further improve the accuracy of the determination.

FIG. 5 shows the operation of the electrolyte analysis device according to the present example. FIG. 5A is a flowchart showing the flow of the operation executed when the bubble size detected during the first liquid supply operation is determined to be abnormal. FIGS. 5B and 5C are diagrams showing the positions of the detector 102 and bubbles in the flow path.

FIGS. 5B and 5C show the flow path of the internal standard solution as an example of the flow path, and the internal standard solution bottle 3, the filter 16, the detector 102, the solenoid valve 30, the internal standard solution syringe 8, the solenoid valve 19, and the dilution tank 11 are shown in relation to the flow path. In the following description, an internal standard solution will be used as an example of the liquid. However, the following description also applies to the flow path of the diluent and the flow path of the reference electrode solution.

Since it is assumed that bubbles that could not be removed by the filter 16 (and the degassing mechanism 7 if present) are detected by the detector 102 in the flow path, more stable bubble size determination becomes possible if the detector 102 is installed near the filter 16 (and the degassing mechanism 7 if present).

During the first liquid supply operation, if it is determined in the process of FIG. 5A that the bubble size is abnormal (step S21), the liquid supply unit ends the first liquid supply operation and executes an operation of reversely feeding the internal standard solution (reverse liquid supply operation) using the internal standard solution syringe 8 or the like (step S22). That is, the internal standard solution is sent back to the internal standard solution bottle 3 side. By this operation, as shown in FIG. 5C, the bubbles are sent back to the upstream side from the detector 102.

Next, the liquid supply unit executes an operation of feeding the liquid via the detector 102 (second liquid supply operation) in the flow path (step S23). The second liquid supply operation is performed in the same direction as the first liquid supply operation. By the second liquid supply operation, the bubbles pass through the detector 102 again and are sent to the position shown in FIG. 5B. The second liquid supply operation is a liquid supply operation that maintains the flow velocity of the liquid passing through the detector 102 within a predetermined flow velocity range among the operations of the detector 102.

"Maintaining the flow velocity within a predetermined flow velocity range" means, for example, maintaining the flow velocity at a constant value and includes maintaining the flow velocity within an allowable range that does not substantially affect the detection performance of the detector 102. Specific values of this allowable range can be appropriately determined by person skilled in the art.

For example, when the operation speed of the liquid supply unit is a constant speed as shown in FIG. 4A, the timing of the start and end of the operation is controlled so as not to be included in the bubble detection time zone by the detector 102. Further, when the operation speed of the liquid supply unit includes the acceleration portion and the deceleration portion as shown in FIG. 4B, the acceleration portion and the deceleration portion are controlled so as not to be included in the bubble detection time zone by the detector 102.

The details of such control of the liquid supply unit can be appropriately designed by those skilled in the art. For example, it is possible to determine the time zone T6 in which the detector 102 operates during the second liquid supply operation based on the amount of the internal standard solution sent in the first liquid supply operation, the amount of the internal standard solution sent back in the reverse liquid supply operation, and the time zone T5 during which the detector 102 detects bubbles in the first liquid supply operation.

As a more specific example, first, the passing time zone T7 in which the bubbles are expected to pass through the detector 102 in the second liquid supply operation is calculated. Then, the above time zone T6 is determined as a detection time zone including the passing time zone T7, the margin time before the passing time zone T7, and the margin time after the passing time zone T7. The detector 102 can be operated in this time zone T6. As described above, the second liquid supply operation is executed to maintain the flow velocity constant (or within a predetermined flow velocity range) during the time zone T6.

In this way, due to the reverse liquid supply operation and the second liquid supply operation related to the reconfirmation, the portion where the flow velocity is not stable and the detection timing of the detector 102 do not overlap, and the sizes of the bubbles can be determined more reliably at the timing at which the flow velocity is stable.

The determination unit determines whether or not the size of the bubbles detected during the second liquid supply operation is normal (step S24). This determination can be made based on the operation speed of the liquid supply unit and the detection time of bubbles, as in the determination in the first liquid supply operation, for example. For example, if no bubbles are detected or if the bubble detection time is less than the threshold time, the bubble size is determined to be normal, and if the bubble detection time is equal to or longer than the threshold time, the bubble size is determined to be not normal (or abnormal). In this way, the bubble size is re-determined. However, the determination in step S24 may be made not based on the operation speed of the liquid supply unit and the detection time of bubbles.

If the bubble size is determined to be normal, the liquid (reagent) is used as it is and the measurement operation is continued (step S25). The operation in this case can be designed in the same manner as a known automated analysis device. In this case, even if bubbles are present, the influence on the analysis result is considered to be small.

If it is determined that the bubble size is abnormal, the liquid (reagent) is discarded (step S26). That is, the reagent becomes unusable. The operation in this case can also be designed in the same manner as a known automated analysis device. In this case, since the analysis operation is not executed, it is possible to avoid the occurrence of an error due to bubbles.

As described above, according to the electrolyte analysis device according to Example 2, when bubbles of abnormal sizes are detected, the bubble size can be re-determined with higher accuracy by stabilizing the flow velocity and performing re-feeding.

Example 3

In Example 3, Example 1 is modified so that reverse liquid supply and re-feeding of the reagent are performed to always provide two determination opportunities.

FIG. 6 is a schematic diagram showing the movement of the liquid in Example 3. FIGS. 6A, 6B, 6C, and 6D show the positions of the detectors 102 in the flow paths. The "liquid supply direction" indicates a direction from the reagent container (the internal standard solution bottle 3, and the like) toward the measurement point (the dilution tank 11, the ISE electrode 1, the reference electrode 2, and the like). In Example 3, the liquid is passed through the detector 102 a plurality of times before using the reagent.

The electrolyte analysis device according to the present example uses a predetermined amount of liquid as a reagent for one analysis operation. Reagent R1 (first liquid portion), reagent R2 (second liquid portion), and reagent R3 (third liquid portion) of FIG. 6 are liquid portions each containing a predetermined amount of liquid used for one analysis operation. The reagents R1 to R3 do not need to be physically separated from each other.

First, as shown in FIG. 6A, the liquid amount corresponding to a plurality of times (three times in this example) is sucked. Next, as shown in FIG. 6B, the liquid supply unit feeds the reagent R1 and the reagent R2 via the detector 102 in the first liquid supply operation. Next, as shown in FIG. 6C, the liquid supply unit executes a reverse liquid supply operation in which the reagent R2 is reversely sent via the detector 102.

Next, as shown in FIG. 6D, the liquid supply unit executes the second liquid supply operation in which the reagent R2 is sent via the detector 102. In the example of FIG. 6, since the reagent R3 exists after the reagent R2, the reagent R2 and the reagent R3 are sent in the second liquid supply operation. The second liquid supply operation for the reagent R2 corresponds to the first liquid supply operation for the reagent R3. After that, the reagent R3 is further subject to the reverse liquid supply operation and the second liquid supply operation.

By these liquid supply operations, the reagent R2 passes through the detector 102 three times. Here, the reagent R2 is controlled to pass through the detector 102 at a constant speed in at least one of the first liquid supply operation, the reverse liquid supply operation, and the second liquid supply operation. That is, in at least one of the first liquid supply operation, the reverse liquid supply operation, and the second liquid supply operation, the liquid supply unit maintains the flow velocity of the reagent R2 passing through the detector 102 within a predetermined flow velocity range (or a constant value) during the operation of the detector 102. Specific timing control and the like at this time can be appropriately determined by those skilled in the art. For example, the same method as in Example 2 may be used for designing based on appropriate parameters.

The determination unit determines the sizes of bubbles when each reagent passes through the detector 102 within a predetermined flow velocity range. For example, the sizes of the bubbles contained in the reagent R2 are determined when the reagent R2 passes through the detector 102 within a predetermined flow velocity range.

FIG. 6 shows only the operation when the bubble size is determined to be normal, but when the bubble size is determined to be abnormal, an operation such as discarding the reagent may be performed.

For example, if the reagent R1 is controlled to pass through the detector 102 at a constant speed in the first liquid supply operation, the reagent R2 may not reach a constant speed in the first liquid supply operation. In this case, the reagent R2 is controlled to have a constant speed in the reverse liquid supply operation or the second liquid supply operation. In particular, when the reagent R2 has a constant speed in the reverse liquid supply operation, it is not necessary to set the reagent R2 to a constant speed in the second liquid supply operation and the reagent R3 can be controlled to have a constant speed.

On the other hand, when it is not necessary to control the reagent R1 at a constant speed in the first liquid supply operation, the reagent R2 can be controlled to have a constant speed in the first liquid supply operation. In this case, it is not necessary to set the reagent R2 at a constant speed in the reverse liquid supply operation and the second liquid supply operation.

As described above, according to the electrolyte analysis device according to Example 3, the bubble size can always be determined within a predetermined flow velocity range, and thus, the accuracy of the determination is higher.

Generally, the measurement operation of the electrolyte analysis device is scheduled when the measurement item is requested. According to this schedule, the control device 29 controls the operation of each mechanism and executes the measurement operation. Therefore, when it is determined that the bubble size detected by the detector 102 is abnormal, it is impossible to measure the specimen whose schedule is set to measure using the reagent in which bubbles are detected. If a request for another measurement item is made, the specimen is sent to a device (not shown) for collecting the sample after the measurement is performed for that item. On the other hand, if there is no request for another measurement item, the specimen is not used and returned to the device for collecting the sample, and a request for re-measurement is required.

On the other hand, according to Examples 1 to 3, it becomes possible to determine whether or not the reagent can be used relatively easily and accurately before the measurement operation using a target specimen. Therefore, even if it is determined that the reagent cannot be used, it is possible to prevent the situation where such a reagent is added to the specimen and stop the movement of the specimen until a usable reagent is supplied. Therefore, rescheduling can be performed so that the measurement can be performed normally, the effort of requesting the re-measurement can be eliminated, and the re-obtaining of the specimen from the patient becomes unnecessary.

In this way, even if bubbles of abnormal sizes are incorporated or generated in the reagent flow path, inappropriate analysis operation can be prevented in advance by determining the presence or absence or sizes of bubbles relatively easily and accurately.

In Examples 1 to 3, the sizes of bubbles are determined for all three types of liquids, i.e., the internal standard solution, the diluent, and the reference electrode solution. However, only one or more liquids may be used, and the bubble size determination may be performed for only one type. Moreover, 4 or more types of liquids may be used.

Further, in an automated analysis device such as an electrolyte analysis device, a portion excluding a configuration related to bubble size determination (for example, a portion related to a measurement operation or an analysis operation) can be configured in the same manner as a known device.

REFERENCE SIGNS LIST

1: ISE electrode
2: Reference electrode
3: Internal standard solution bottle
4: Diluent bottle
5: Reference electrode solution bottle
6: Suction nozzle
7: Degassing mechanism
8: Internal standard solution syringe (Liquid supply unit)
9: Diluent syringe (Liquid supply unit)
10: Sipper syringe (Liquid supply unit)
11: Dilution tank
12: Preheat
13: Sipper nozzle
14: Sample probe
15: Sample container
16: Filter
17 to 22 and 30: Solenoid valves (Liquid supply unit)
23: Pinch valve
24: Diluent nozzle
25: Internal standard solution nozzle
26: First waste liquid nozzle
27: Voltmeter
28: Amplifier
29: Control device (Determination unit, Control unit)
33: Vacuum pump
34: Vacuum bottle
35: Waste liquid receiver
36: Second waste liquid nozzle
102: Detector (Detection unit)
R1: Reagent (First liquid portion)
R2: Reagent (Second liquid portion)
R3: Reagent

The invention claimed is:

1. An automated analysis device comprising:
a bottle containing a first liquid;
a syringe;
a first flow path, through which the first liquid flows, connecting the bottle with the syringe;
a detector which detects bubbles included in the first liquid in the first flow path;
a tank coupled to the syringe via a second flow path through which the first liquid flows;
a controller coupled to the detector and the syringe, the controller configured to:
operate the syringe to perform a first liquid supply operation,
determine whether bubbles are included in the first liquid,
in response to determining that bubbles are included in the first liquid:
determine a speed of operation of the syringe,
determine a threshold time based on the determined speed of the operation of the syringe,
determine whether a time during which the bubbles are detected by the detector is less than the determined threshold time,
upon determining the time during which the bubbles are detected by the detector is less than the determined threshold time, determine a size of the bubbles to be normal,
upon determining the time during which the bubbles are detected by the detector is greater than or equal to the determined threshold time, determine that the size of the bubbles is abnormal, and control at least the operation of the syringe based on whether the size of the bubbles is normal or abnormal.

2. The automated analysis device according to claim 1, wherein, controller is configured to:

upon determining that the bubble size is not normal, cause at least the syringe to execute a second liquid supply operation via the detection unit after the first liquid supply operation, and determine whether the bubble size after the second liquid supply operation is normal.

3. The automated analysis device according to claim 2, wherein the controller is configured to:

upon determining that the bubble size is abnormal, cause the syringe to execute a reverse liquid supply operation in which the liquid is reversely fed in at least the first flow path, and wherein the second liquid supply operation is a liquid supply operation in which a flow velocity of the liquid that passes through the detector is maintained within a predetermined flow velocity range during the operation of the detector.

4. The automated analysis device according to claim 1, wherein the controller is configured to:

determine whether the bubble size is normal based on a cross-sectional area of the first flow path.

5. The automated analysis device according to claim 3, wherein a time zone at which the detector operates during the second liquid supply operation is determined based on an amount of the liquid supplied in the first liquid supply operation, an amount of the liquid reversely fed in the reverse liquid supply operation, and a time zone at which the detector detects the bubbles in the first liquid supply operation.

6. The automated analysis device according to claim 1, wherein the automated analysis device uses a predetermined amount of a liquid for one analysis operation, wherein the syringe supplies a first liquid portion including the predetermined amount of liquid and a second liquid portion including the predetermined amount of liquid via the detector in the first liquid supply operation, wherein the controller is configured to:

cause the syringe to execute a reverse liquid supply operation in which the second liquid portion is reversely fed via the detector after the first liquid supply operation, cause the syringe to execute a second liquid supply operation in which the second liquid portion is supplied via the detector after the reverse liquid supply operation, and cause the syringe to maintain a flow velocity of the second liquid portion that passes through the detector within a predetermined flow velocity range during operation of the detector, in at least one of the first liquid supply operation, the reverse liquid supply operation, and the second liquid supply operation.

* * * * *